(12) United States Patent
Lantermann et al.

(10) Patent No.: US 10,166,012 B2
(45) Date of Patent: Jan. 1, 2019

(54) HOLDING DEVICE FOR A SURGICAL INSTRUMENT

(71) Applicant: DEUTSCHES ZENTRUM FÜR LUFTUND RAUMFAHRT E.V., Köln (DE)

(72) Inventors: Sophie Lantermann, Munich (DE); Ulrich Seibold, Burnaby (CA); Ulrich Hagn, Munich (DE); Thomas Staebler, Tuebingen (DE)

(73) Assignee: DEUTSCHES ZENTRUM FUER LUFT-LUND RAUMFAHRT E.V., Cologne (DE)

( * ) Notice: Subject to any disclaimer, the term of this patent is extended or adjusted under 35 U.S.C. 154(b) by 291 days.

(21) Appl. No.: 14/891,138

(22) PCT Filed: Apr. 28, 2014

(86) PCT No.: PCT/EP2014/058599
§ 371 (c)(1),
(2) Date: Nov. 13, 2015

(87) PCT Pub. No.: WO2014/183980
PCT Pub. Date: Nov. 20, 2014

(65) Prior Publication Data
US 2016/0106407 A1 Apr. 21, 2016

(30) Foreign Application Priority Data
May 16, 2013 (DE) ........................ 10 2013 209 122

(51) Int. Cl.
*A61B 19/00* (2006.01)
*A61B 17/00* (2006.01)
*B25J 15/04* (2006.01)
*A61B 34/30* (2016.01)

(52) U.S. Cl.
CPC .... *A61B 17/00234* (2013.01); *A61B 19/2203* (2013.01); *A61B 19/26* (2013.01);
(Continued)

(58) Field of Classification Search
CPC .... A61B 17/00234; A61B 19/22; A61B 34/30
See application file for complete search history.

(56) References Cited

U.S. PATENT DOCUMENTS

2006/0108958 A1 5/2006 Brenner
2007/0089557 A1* 4/2007 Solomon ............... B25J 9/1045
74/490.01
(Continued)

FOREIGN PATENT DOCUMENTS

DE 102009060987 A1 6/2011
WO 2009061915 A2 5/2009
(Continued)

OTHER PUBLICATIONS

Guthart et al; "The Intuitive Telesurgery System: Overview and Application"; Robotics and Automation, 2000. Proceedings. ICRA '00. IEEE International Conference on (vol. 1 ); Apr. 24, 2000; pp. 1-4.
(Continued)

*Primary Examiner* — Melanie Tyson
(74) *Attorney, Agent, or Firm* — Ohlandt, Greeley, Ruggiero & Perle, LLP

(57) ABSTRACT

A holding device for surgical instruments, in particular for minimally invasive surgery, is provided. The device includes a holding arm that holds an instrument support at the distal end of the holding arm. The instrument support can have which a surgical instrument is mounted thereon. The surgical instrument is operated by way of a drive device. To permit a simple replacement of the instrument support, the drive device is connected to the holding arm by way of a holding device, such that the drive device can easily be changed from a drive position to a replacement position.

14 Claims, 3 Drawing Sheets

(52) U.S. Cl.
CPC .............. *A61B 34/30* (2016.02); *B25J 15/04* (2013.01); *A61B 2017/00477* (2013.01)

(56) References Cited

U.S. PATENT DOCUMENTS

| | | | |
|---|---|---|---|
| 2008/0188868 A1* | 8/2008 | Weitzner | A61B 1/0014 606/130 |
| 2011/0277775 A1 | 11/2011 | Holop et al. | |
| 2012/0065467 A1 | 3/2012 | Moll et al. | |
| 2012/0289973 A1 | 11/2012 | Prisco et al. | |
| 2012/0330286 A1 | 12/2012 | Seibold et al. | |
| 2013/0012959 A1 | 1/2013 | Jinno | |

FOREIGN PATENT DOCUMENTS

| | | |
|---|---|---|
| WO | 2011040813 A1 | 4/2011 |
| WO | 2012071408 A1 | 5/2012 |
| WO | 2013018926 A1 | 2/2013 |

OTHER PUBLICATIONS

Hagn et al; "DLR MiroSurge: a Versatile system for research in Endoscopic Telesurgery"; Int J Cars; May 21, 2009; pp. 1-10.
International Search Report dated Aug. 4, 2014 for PCT application No. PCT/EP2014/058599.
Written Opinion of the International Search Authority dated Nov. 16, 2015 for PCT Application No. PCT/EP2014/058599.
International Preliminary Report on Patentability dated Nov. 17, 2015 for PCT Application No. PCT/EP2014/058599.

* cited by examiner

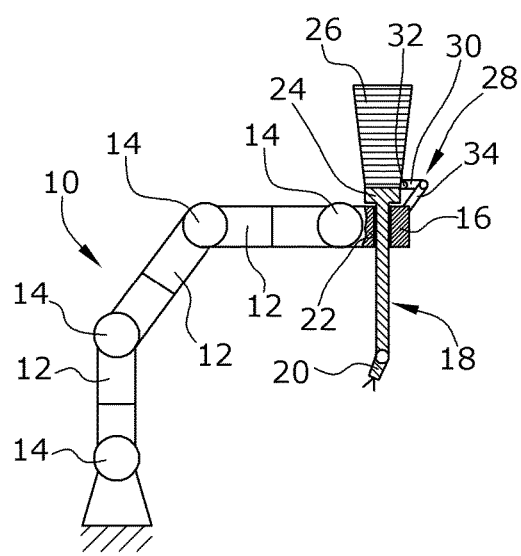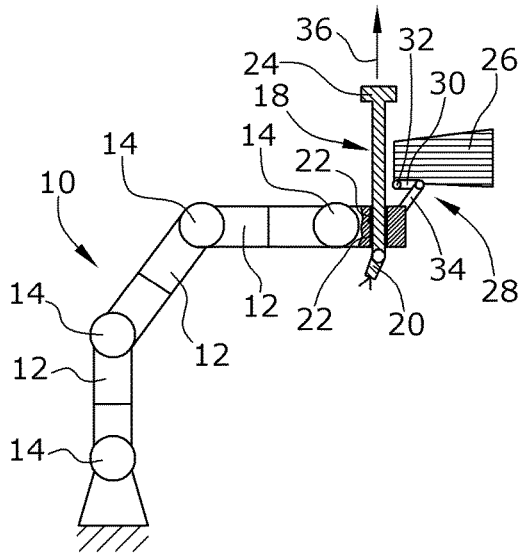
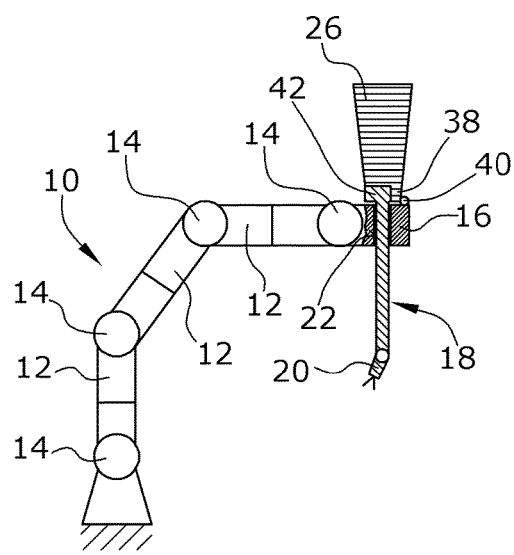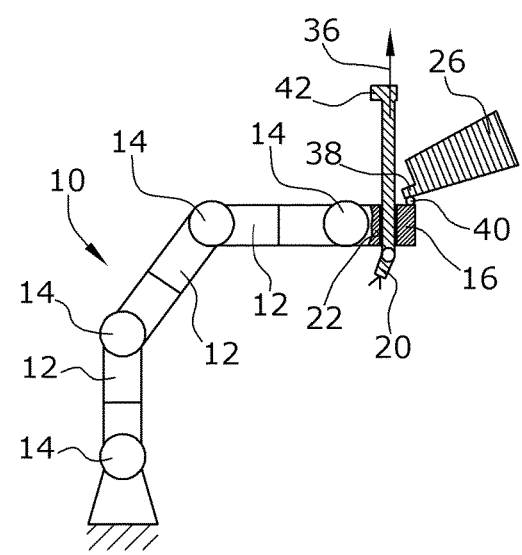

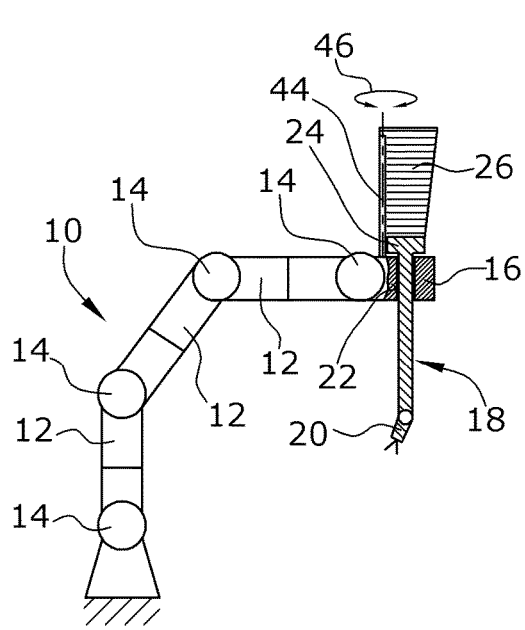
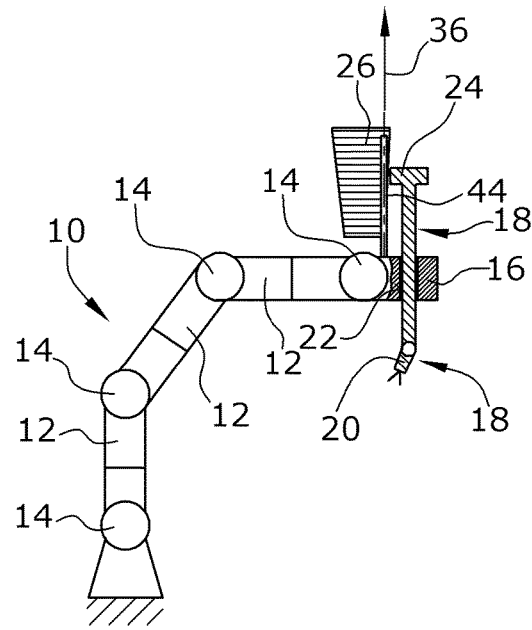
Fig.3a    Fig.3b
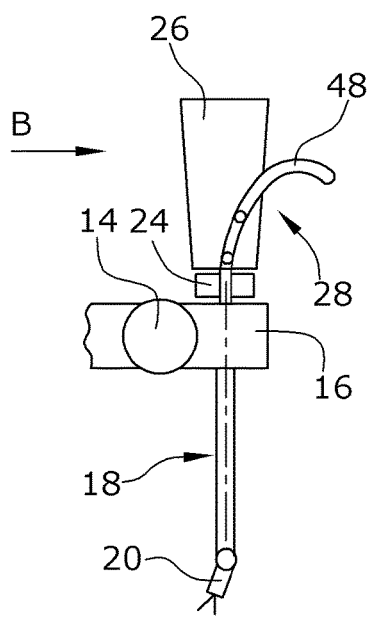
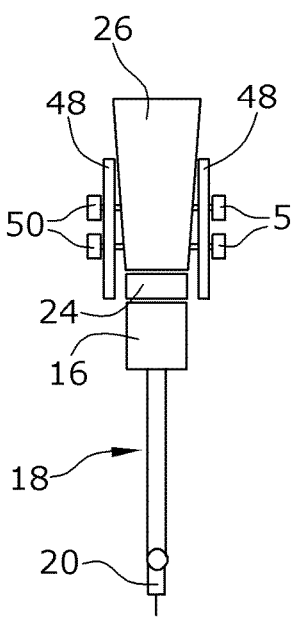
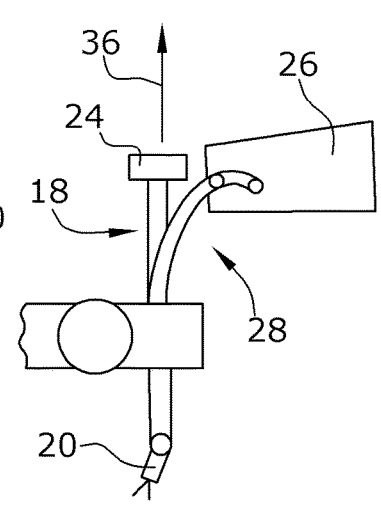
Fig.4a    Fig.4b    Fig.4c

HOLDING DEVICE FOR A SURGICAL INSTRUMENT

BACKGROUND

1. Field of the Disclosure

The disclosure relates to a holding device for a surgical instrument, particularly for an instrument used in minimally invasive surgery.

2. Discussion of the Background Art

In minimally invasive surgery surgical instruments are introduced into the interior of a patient's body via so-called trocars. The trocars keep small incisions in the skin of a patient open so that long, usually rod-shaped instruments can be introduced into the site. Various instruments are required during a surgical operation so that a change of instruments is necessary. This is required in particular because only the smallest possible number of trocars is provided. In robotic surgery the surgical instrument is held and guided by a robot arm. A corresponding holding arm, which in particular comprises a plurality of elements connected through hinges, carries an instrument support which supports the surgical instrument at its distal end. The surgical instrument is operated via traction cables, shafts and the like provided in the instrument support, for example. The operation is performed by a drive device.

From Guthart, G S and Salisbury, J K: The Intuitive Telesurgery System: Overview and Application, Proceedings of ICRA 2000, it is known to arrange the drive device inside the holding arm. To exchange the surgical instrument, the instrument support is detached from the holding arm and is then either replaced with a new instrument support carrying a new surgical instrument or the surgical instrument on the instrument support will be exchanged. In this case, the instrument support is pivoted, whereby the instrument is pivoted inside the patient. The surgical instrument may possibly be connected immediately with the holder arm so that an instrument support may be omitted. This pivoting may lead to injuries. Further, a connection of the drive device with the instrument support has to be realized via intermediate elements.

From Hagn, U. et al.: DLR MiroSurge: a versatile system for research in endoscopic telesurgery, International journal of computer assisted radiology and surgery, 5, 2, pages 183-193, 2010 Springer, it is further known to exchange the drive device together with the instrument support or together with the surgical instrument. This is advantageous in that a rigid connection with the instrument support is possible and that, further, the drive device matched with the corresponding instrument support and the surgical instrument can always be provided. On the other hand, this is advantageous in that the components are more expensive, since a respective drive device is connected with each instrument support. In this context, it is well possible to separate the drive devoice from the instrument support and to subsequently connect the drive device with the new instrument support, yet this requires a two-handed and time consuming manipulation. The surgical instrument may be formed integrally with the instrument support or the instrument support may be omitted so that the surgical instrument is directly connected with the drive device.

It is an object of the disclosure to provide a holding device for surgical instruments, which allows for a simple exchange of instrument supports. Further, it is an object of the disclosure to provide a simplified method for changing a surgical element on a holding device.

SUMMARY

The present holding device for surgical instruments, which is particularly suited for use in minimally invasive surgery, comprises a holding arm such as a robot arm, in particular a robot arm with a plurality of hinges. The instrument support is carried by the holding arm. A surgical instrument is arranged at the distal end of the instrument support. The surgical instrument may be designed with the instrument support such that it is exchangeable or it may be formed integrally with the instrument support. Here, the surgical instrument extends over a larger area and is not only arranged at the distal end of the instrument support. The surgical instrument itself may therefore be made very small and may be connected with the distal end of the instrument support in an exchangeable manner. On the other hand, an integral design is possible so that the instrument support is formed integrally with the surgical instrument, or the instrument support is omitted so that the surgical instrument is connected directly with the holding arm. The instrument support may be introduced into the interior of a patient via a trocar in order to perform surgery. Further, a drive device for actuating the surgical instrument is connected with the instrument support, in particular in a detachable manner. According to the disclosure, the drive device is connected with the holding arm via a holding device. Thereby, it is possible to move the drive device from a driving position to an exchanging position. In the driving position the drive device is connected with the instrument support, and thus with the surgical instrument, in order to actuate the surgical instrument. In the exchanging position the drive device is uncoupled from the instrument support in such a manner that it is possible to exchange the instrument support. Thus, the holding device serves, on the one hand, to hold or fix the drive device on the holding arm and, on the other hand, to provide a detachable connection with the instrument support or the surgical instrument.

To exchange the instrument support, the drive device can be moved to an exchanging position without having to be detached completely from the holding arm. In this position in which the drive device is uncoupled, it is then possible to replace the instrument support in a simple manner. After the instrument support has been exchanged, i.e. after the new instrument support is again connected with the holding arm, the drive device is returned to the driving position from the exchanging position by means of the holding device, so that the drive device is again coupled with the instrument support in a simple manner.

Possibly, the instrument support and the holding arm may also be formed integrally.

In this regard it is particularly preferred that the holding device comprises a pivot element. Using the pivot element, it is possible to pivot or turn the drive device between the driving and exchanging positions. Here, it is preferred that coupling or uncoupling is performed automatically upon pivoting or turning.

In a further preferred embodiment the holding device comprises a sliding element so that the drive device can be shifted between the two positions, wherein a coupling or uncoupling is preferably also performed automatically.

The sliding element may preferably comprise a guiding rail in order to guarantee a defined guiding when the drive device is moved from one position to the other position. In this regard, the guiding rail may have a curved guide track, for example, in which guide pins may slide that are connected with the drive device.

Of course, it is also possible to combine one or a plurality of pivot elements with one or a plurality of sliding elements.

In a preferred development of the disclosure the holding device comprises at least one fixing element for fixing the drive device in the driving position and/or in the exchanging position. Possibly, a respective fixing element is provided for each position. The fixing element may be a locking element, e.g. a holding element formed by a magnet, or the like. If, for example, a fixing element is provided for fixing the drive device in the exchanging position, it is thereby ensured that no inadvertent positional changes of the drive device occur while the instrument support is exchanged. This could lead to vibrations and thus to injuries to the patient etc. A fixing element, by which the drive device is retained in the driving position, has the advantage that an unintentional change of the drive device's position during surgery is avoided.

In a further preferred embodiment the holding device comprises at least one damping element. The damping element dampens the movement of the drive device during a change of the position of the drive device. Preferably, at least one damping element is provided by which the movement of the drive device to the driving position and/or the exchanging position is damped. Possibly, a separate damping element may be provided for each position. By providing at least one damping element, vibrations and the resulting disadvantages are avoided when the position of the drive device is changed.

In a particularly preferred embodiment, the instrument support is directly connected with the drive device in the driving position, particularly by means of plug contacts. Therefore, a connection via an intermediate element is not required, which would be necessary if the drive device were arranged more distantly on the robot arm. It is possible to thereby avoid in particular inaccuracies in the transmission of movements.

In another preferred embodiment it is possible to connect an auxiliary drive device with the holding device. In this manner, it is possible to provide additional drives for special instruments in a simple manner, if necessary. For example, some instruments require more powerful drives.

In a holding device for surgical instruments, which is an independent disclosure, a recess is provided in the drive device instead or in addition to the above holding device of the present disclosure, the recess being provided to receive the instrument support. Owing to such a recess, which in particular is a plug-in opening, it is possible to fixedly connect the drive device with the holding arm. The holding arm is exchanged by pulling the same out of the recess, in particular the plug-in opening, and by inserting the new instrument support. In this embodiment as well, it is particularly preferred that an immediate coupling can be made between the instrument support and the drive device, in particular by means of plug contacts.

Thus, it is an essential feature of the above disclosures that the driving unit can be separated from the instrument support. These components are not fixedly connected with each other. Besides the motor, control electronics may also be integrated in the driving unit. Since the instrument support is an instrument support particularly intended for use in minimally invasive surgery, it is of an elongate and thin shape and is introduced into the patient. During surgery it is necessary to change surgical instruments supported by the instrument support. For example, it is necessary to change from a needle holder to a pair of scissors or a tissue gripper. Due to the possibility to move the drive device to an exchanging position, it is possible according to the disclosure that the drive device remains connected with the holding arm and the instrument support, which is configured to be independent of the drive device, can thus be exchanged. This makes for a substantial saving of costs, since not every instrument support has to be provided with a drive device, but one drive device can be used for a plurality of instrument supports. Further, due to the present connection between the driving unit and the holding arm, it is advantageous that the drive device does not have to be deposited so that no risk of contamination is created either. The holding device of the present disclosure allows for a fast and safe exchange of the instrument support.

Thus, it is an essential aspect of the disclosure that the drive device can, on the one hand, be advantageously coupled with the instrument support in a simple and safe manner and, on the other hand, is connected with the holding arm such that it is possible to move the drive device to the exchanging position in a simplified manner.

The disclosure further relates to a method for exchanging a surgical instrument, in particular a surgical instrument for use in minimally invasive surgery on a holding device. The holding device comprises at least one instrument support carried by a holding arm, the instrument support being connected with a driving unit in order to actuate a surgical instrument connected with the instrument support. The holding device is preferably configured in an advantageous manner as explained above. According to the method of the present disclosure, the driving unit is moved from a driving position to an exchanging position. This may be effected by pivoting, sliding and the like as has been described above in particular with reference to the holding device. In the exchanging position the instrument support is replaced, while, in the exchanging position, the driving unit remains connected with the holding arm.

Preferably, the instrument support is separated from a drive device for example prior to the drive device being moved to the exchanging position. It is preferred that this separation occurs during or by the movement itself. It is particularly preferred that the electric or mechanical contacts between the drive device and the instrument support are disconnected by moving the drive device to the exchanging position. This allows for a simple and fast handling and exchange of the instrument support.

In particular, the method of the present disclosure is advantageously embodied as described above with respect to the holding device.

The following is a detailed description of the disclosure with reference to preferred embodiments and to the accompanying drawings.

BRIEF DESCRIPTION OF THE DRAWINGS

In the Figures:
FIG. 1a is a schematic illustration of a first embodiment in a driving position,
FIG. 1b is a schematic illustration of the first embodiment of FIG. 1a in an exchanging position,
FIG. 2a is a schematic illustration of a second embodiment in a driving position,
FIG. 2b is a schematic illustration of the second embodiment of FIG. 2a in an exchanging position,
FIG. 3a is a schematic illustration of a third embodiment in a driving position,
FIG. 3b is a schematic illustration of the third embodiment of FIG. 3a in an exchanging position,
FIG. 4a is a schematic illustration of a fourth embodiment in a driving position,
FIG. 4b is an illustration of the embodiment of FIG. 4a in side elevational view in the direction of the arrow B in FIG. 4a, FIG. 4c is a schematic illustration of the fourth embodiment of FIGS. 4a and 4b in an exchanging position.

DETAILED DESCRIPTION OF THE PREFERRED EMBODIMENT

Figure 5A:
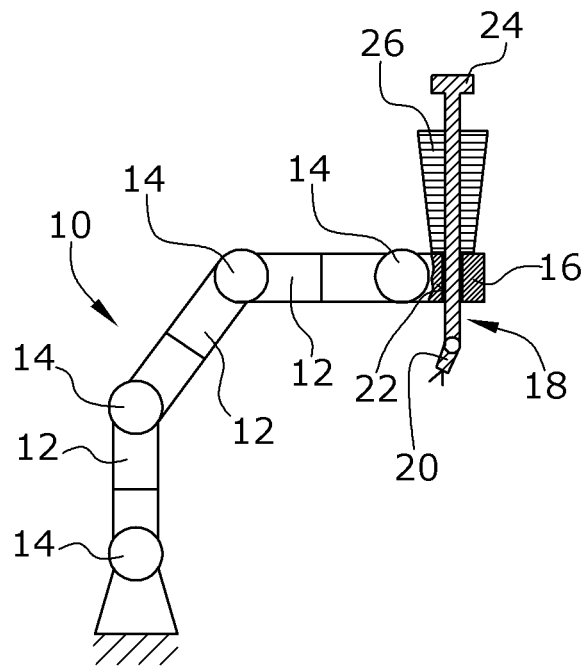
FIG. 5a is a schematic illustration of a fifth embodiment in a driving position.

In the preferred embodiments of the disclosure illustrated, similar and identical components are identified by the same reference numerals.

The holding devices comprise a holding arm 10 which, in the embodiment illustrated, is configured as a robot arm. The holding arm 10 comprises a plurality of elements 12 connected with each other via hinges 14. A receiving element 16 of the holding arm is hingedly connected with the last hinge 14. The receiving element 16 serves to receive the instrument holder 13 that carries a surgical instrument 20 at its distal end. The instrument support 18 is received by means of a plug-in opening 22 provided in the receiving element 16. Further, the instrument support 18 comprises a head element 24 which is connected with a drive device 26 in particular by means of plug contacts. The drive device 26 is connected with the holding arm 10 or the receiving element 16 of the holding arm 10 by means of a holding device 28.

In the first embodiment illustrated, the holding element 28 comprises a pivot element 30. In the embodiment illustrated, the pivot element 30 is connected with the drive device 26 via a hinge 32. Further, the holding device 28 of the embodiment illustrated in FIGS. 1a and 1b comprises a spacer 34. The spacer 34 serves to allow the drive device 26 to be arranged, when in the driving position (FIG. 1a), in an orientation such that the head 24 in FIG. 1a is arranged below the drive device 26 and is securely connected with the drive device 26.

To exchange the instrument support 18, the drive device 26 is pivoted to the position illustrated in FIG. 1b. It is then possible to pull the instrument support 18 upward out of the receiving element 16 of the holding arm 10 in the direction of the arrow 36 in FIG. 1b. After having replaced the instrument 20 at the distal end of the instrument support 18 or after having replaced the complete instrument support, the same may be reinserted into the opening 22 and the drive device 26 may be pivoted back to the driving position (FIG. 1a) from the exchanging position (FIG. 1b).

It is possible to provide damping elements, which are not illustrated, in order to avoid or at least dampen vibrations in the holding arm when the drive device 26 is pivoted to the different positions. Further, fixing elements may be provided which preferably fix the drive device in both positions.

In the embodiment illustrated in FIG. 2, the drive device 26 or the housing of the drive device 26 comprises a protrusion 38. The latter is directed towards the receiving element 16. In this embodiment, the holding element is designed as a hinge 40 arranged between the protrusion 38 and the receiving element 16. Further, a head 42 of the instrument support 18 is designed such that, in the driving position (FIG. 2a), the protrusion 38 is arranged beside the head 42. This allows for a more compact structure. Further, the holding device may be designed in a simpler fashion.

Similar to the first embodiment, the drive device 26 is adapted to be pivoted to an exchanging position (FIG. 2b), owing to the hinge 40 provided, so that the instrument support 18 can be pulled out of the receiving element 16 in the direction of an arrow 36.

In the embodiment illustrated in FIGS. 3a and 3b, a pivot axis 44 is provided that is connected with the receiving element 16. This allows the drive device 26 to be pivoted as illustrated by the arrow 46. To exchange the instrument support 18 (FIG. 3b), the drive device 26 is pivoted about the pivot axis 44 to the position illustrated in FIG. 3b. The instrument support 18 is then exchanged as described above with reference to the foregoing two embodiments.

Another preferred embodiment is illustrated in FIGS. 4a to 4c. This embodiment comprises two opposite guide rails 48 serving as the holding device 28. In each of the two guide rails 48, two guide pins 50 are arranged which are connected with the drive device 26. Due to the curved design of the two guide rails 48, it is possible to move the drive device from the driving position (FIGS. 4a and 4b) to the exchanging position (FIG. 4c). As described above, it is then again possible to exchange the instrument support 18.

It is possible in all embodiments described to provide additional fixing elements or damping elements as described with reference to the embodiment illustrated in FIGS. 1a and 1b.

Figure 5B:
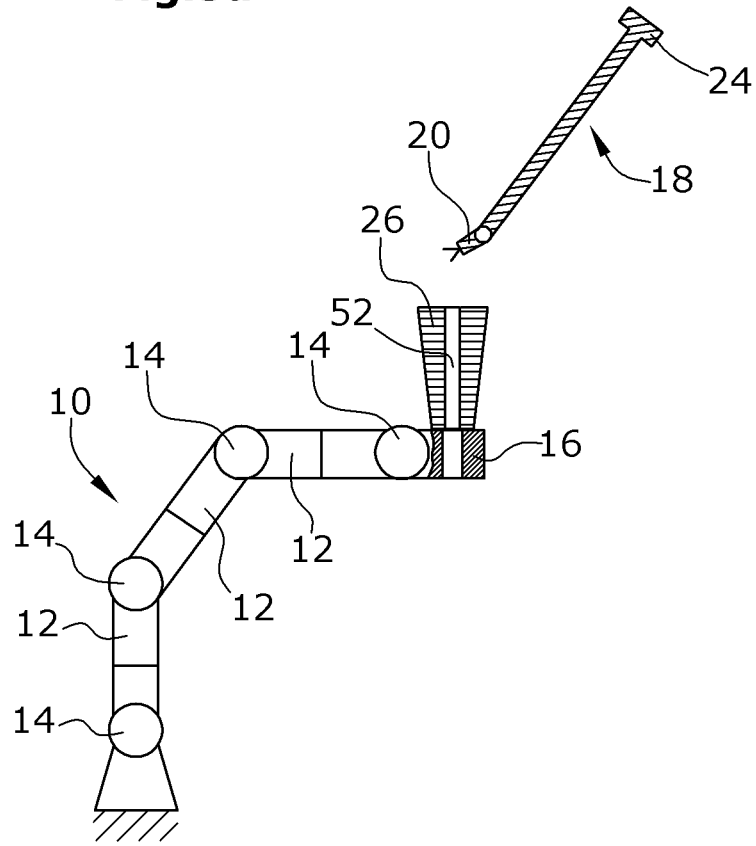
FIG. 5b is a schematic illustration of the fifth embodiment of FIG. 5a in an exchanging position.

In another preferred embodiment (FIGS. 5a and 5b) which is an independent disclosure, similar and identical components are again identified by the same reference numerals. In this embodiment the position of the drive device 26 is not changed. Rather, the same fixedly connected with the receiving element 16. According to the disclosure, this embodiment is provided with a recess or a plug-in opening 52. The same extends longitudinally through the entire drive device 26 and is aligned with the opening provided in the receiving element 16. Thus, exchanging the instrument support 18 is possible by simple insertion into or withdrawal from the plug-in opening 52.

What is claimed is:

1. A holding device for a surgical instrument, comprising:
a holding arm,
an instrument support carried by the holding arm, a distal end of the instrument support being mounted with the surgical instrument, and
a drive unit for operating the surgical instrument, the drive unit being connected with the instrument support, wherein the drive unit is connected with the holding arm via a holding element such that the drive unit is movable from a driving position to an exchanging position, wherein the drive unit, in the driving position, is capable of operating the surgical instrument and, in the exchanging position, is incapable of operating the surgical instrument.

2. The holding device of claim 1, wherein, in the driving position, the drive unit is connected with the instrument support to operate the surgical instrument.

3. The holding device of claim 1, wherein, in the exchanging position, the drive unit is uncoupled from the instrument support to exchange the instrument support.

4. The device of claim 1, wherein, in the exchanging position, the drive unit remains connected with the holding arm.

5. The device of claim 1, wherein the holding element comprises a pivot element for pivoting the drive unit between the driving position and the exchanging position.

6. The device of claim 1, wherein the holding element comprises a sliding element configured to slide the drive unit between the driving position and the exchanging position.

7. The device of claim 1, wherein the holding element comprises at least one fixing element for fixing the drive unit in the driving position and/or the exchanging position.

8. The device of claim 1, wherein, in the driving position, the instrument support is connected directly with the drive unit.

9. The device of claim 1, further comprising an auxiliary drive device connected with the holding device.

10. The device of claim 1, wherein the holding element comprises at least one damping element to dampen movement of the drive unit to the driving position and/or the exchanging position.

11. A method for exchanging a surgical instrument, at the holding device of claim 1, wherein the drive unit is moved from the driving position to the exchanging position, the drive unit remaining connected with the holding arm in the exchanging position.

12. The method of claim 11, wherein the drive unit is separated from the instrument support prior to moving and/or while moving the drive unit to the exchanging position.

13. The method of claim 11, wherein the instrument support is exchanged in the exchanging position without separating the drive unit from the holding arm.

14. A holding device for a surgical instrument, comprising:

a holding arm, an instrument support carried by the holding arm, a distal end of the instrument support being mounted with the surgical instrument, and a drive unit for operating the surgical instrument, the drive unit being connected with the instrument support, wherein the drive unit is connected with the holding arm via a holding element such that the drive unit is movable from a driving position to an exchanging position, wherein the drive unit, in the driving position, is capable of operating the surgical instrument and, in the exchanging position, is incapable of operating the surgical instrument, and wherein the drive unit is uncoupled from the instrument support when in the exchanging position.

* * * * *